United States Patent
Felding

(10) Patent No.: US 7,387,734 B2
(45) Date of Patent: Jun. 17, 2008

(54) METHOD OF OPERATING A DIALYSIS MACHINE

(75) Inventor: Anders Felding, Malmo (SE)

(73) Assignee: Gambro Lundia AB, Lund (SE)

(*) Notice: Subject to any disclaimer, the term of this patent is extended or adjusted under 35 U.S.C. 154(b) by 0 days.

(21) Appl. No.: 10/496,086

(22) PCT Filed: Nov. 22, 2002

(86) PCT No.: PCT/SE02/02145

§ 371 (c)(1),
(2), (4) Date: Oct. 14, 2004

(87) PCT Pub. No.: WO03/043680

PCT Pub. Date: May 30, 2003

(65) Prior Publication Data
US 2005/0040110 A1 Feb. 24, 2005

(30) Foreign Application Priority Data
Nov. 23, 2001 (SE) ................................ 0103907

(51) Int. Cl.
*B01D 61/26* (2006.01)
*B01D 61/30* (2006.01)

(52) U.S. Cl. ............... 210/646; 210/252; 210/321.6; 210/321.71; 210/645; 210/647; 210/739; 604/4.01; 604/5.01; 604/6.09

(58) Field of Classification Search ......... 210/252, 210/321.6, 321.71, 644, 645, 646, 647, 739; 604/4.01, 5.01, 6.09
See application file for complete search history.

(56) References Cited

U.S. PATENT DOCUMENTS

| 4,702,829 A | * | 10/1987 | Polaschegg et al. ...... 210/195.2 |
| 4,784,495 A | * | 11/1988 | Jonsson et al. .......... 366/151.1 |
| 5,259,961 A | * | 11/1993 | Eigendorf ................. 210/646 |
| 5,336,165 A | * | 8/1994 | Twardowski ............... 604/6.1 |
| 5,690,831 A | * | 11/1997 | Kenley et al. ............ 210/646 |
| 5,711,883 A | * | 1/1998 | Folden et al. ............ 210/646 |
| 5,902,476 A |   | 5/1999 | Twardowski |
| 6,132,616 A | * | 10/2000 | Twardowski et al. ....... 210/646 |
| 6,187,198 B1 | * | 2/2001 | Utterberg .................. 210/645 |
| 6,635,026 B1 |   | 10/2003 | Béné |

FOREIGN PATENT DOCUMENTS

| EP | 0 192 588 A1 | 8/1986 |
| EP | 0278100 | 8/1988 |
| EP | 1 097 724 A2 | 5/2001 |
| WO | WO 99/30756 | 6/1999 |
| WO | WO 02/098491 A1 | 12/2002 |

* cited by examiner

*Primary Examiner*—John Kim
(74) *Attorney, Agent, or Firm*—Finnegan, Henderson, Farabow, Garrett & Dunner, L.L.P.

(57) ABSTRACT

A method and apparatus of priming or rinse back of an extracorporeal circuit using a dialysis machine comprising a dialysis liquid preparation system. The dialysis machine is used to prepare a saline solution on-line. The extracorporeal circuit is connected to the dialysis machine and primed with the saline solution.

12 Claims, 1 Drawing Sheet

METHOD OF OPERATING A DIALYSIS MACHINE

TECHNICAL FIELD

The present invention relates to a method of priming or rinse back of an extracorporeal circuit using a dialysis machine. The invention further relates to a dialysis machine comprising means for preparing a saline solution.

BACKGROUND ART

Physiological saline solution (about 9 mg/ml=154 mmol/l) is typically used to prime the extra corporeal circuit before a dialysis patient is connected to the dialysis equipment and to rinse back the blood from the extracorporeal circuit after a dialysis treatment. The purpose of priming the circuit is to remove air from the blood lines and the dialyser as well as to remove possible fragments of remaining sterilising agents or other residuals from the disposables elements, such as bloodlines and dialysers that form the extracorporeal circuit, before the patient is connected. Rinse back is performed to avoid loss of patient blood that would otherwise remain in the extracorporeal circuit.

The conventional way of doing this is to use for instance a 2 liters bag of physiological saline solution of which 1.5 liters is used for priming of the circuit and 0.5 liters is used for rinse back of the blood to the patient after the treatment.

Modern dialysis equipment can perform so called on-line treatments, which means that the substitution fluid for hemofiltration or hemodiafiltration is prepared on-line by means of ultrafiltration of dialysis fluid in several steps to obtain a sterile and pyrogen free fluid.

On-line prepared substitution fluid can be prepared in practically unlimited quantities which means that this fluid also can be used for priming, bolus and rinse back purposes which also is cost saving and convenient from a handling point of view.

However, substitution fluid has to contain a high concentration of bicarbonate. Infusing priming liquid with this volume and composition into the patient often causes problems, e.g. not well feeling. This problem is known from "Gambro AK 200 ULTRA™ operator's manual HCEN9568. Rev 12.1999 and cautioned for in all on-line systems Clinics experiencing such problems often go back to priming with saline from bags.

There is therefore a long felt need for a simple, cheap and practical manner of providing a priming solution.

DISCLOSURE OF THE INVENTION

On this background, it is the object of the present invention to provide a method of priming an extracorporeal circuit of the kind referred to initially, which overcomes the above-mentioned problem. This object is achieved by using a dialysis machine with separate sources of bicarbonate concentrate and sodium chloride concentrate and means to prepare a mix of the liquids from said source of water and said source of sodium chloride concentrate to obtain a saline solution and filling said extracorporeal circuit with said saline solution.

According to an embodiment of the invention the sodium chloride concentrate is prepared by dissolving solid sodium chloride in water. Preferably the arterial line is connected to the dialysis machine through an infusion line which preferably includes an ultrafilter.

According to another embodiment the saline solution comprises minor amounts of other electrolytes and other components for the dialysis liquid, such as potassium, calcium, magnesium, glucose with or without acid such as citric acid, hydrochloric acid and acetic acid. In yet another embodiment, the water from said source of water and/or said saline solution is passed through one or more ultrafilters for removal of bacteria and endotoxins.

Advantageously an indication that the dialysis machine is ready for filling said extracorporeal circuit is provided. Preferably, the saline solution is substantially physiological with a sodium ion concentration about 154 mmol/l.

It is another object of the present invention to provide a dialysis machine that is capable of preparing a saline solution. This object is achieved by providing a dialysis machine with separate sources of bicarbonate concentrate and sodium chloride concentrate and means to prepare a mix of the liquids from said source of water and said source of sodium chloride concentrate to obtain a saline solution.

According to an embodiment of the invention the dialysis machine comprises a conductivity cell downstream of said mixing point. Preferably, the dialysis machine further comprises means to adjust the mixing ratio of said water and said sodium chloride concentrate, preferably in response to a signal from the conductivity cell.

In a further embodiment of the invention, the dialysis machine further comprises an infusion line connected to the outlet of the dialysis machine, said infusion line preferably including an ultrafilter. Preferably, the dialysis machine further comprises at least one ultrafilter in the flow path of said water.

Further objects, features, advantages and properties of the method and dialysis machine according to the invention will become apparent from the detailed description.

BRIEF DESCRIPTION OF THE DRAWINGS

In the following detailed portion of the present description, the invention will be explained in more detail with reference to the exemplary embodiments shown in the drawings, in which.

DETAILED DESCRIPTION

Figure 1:
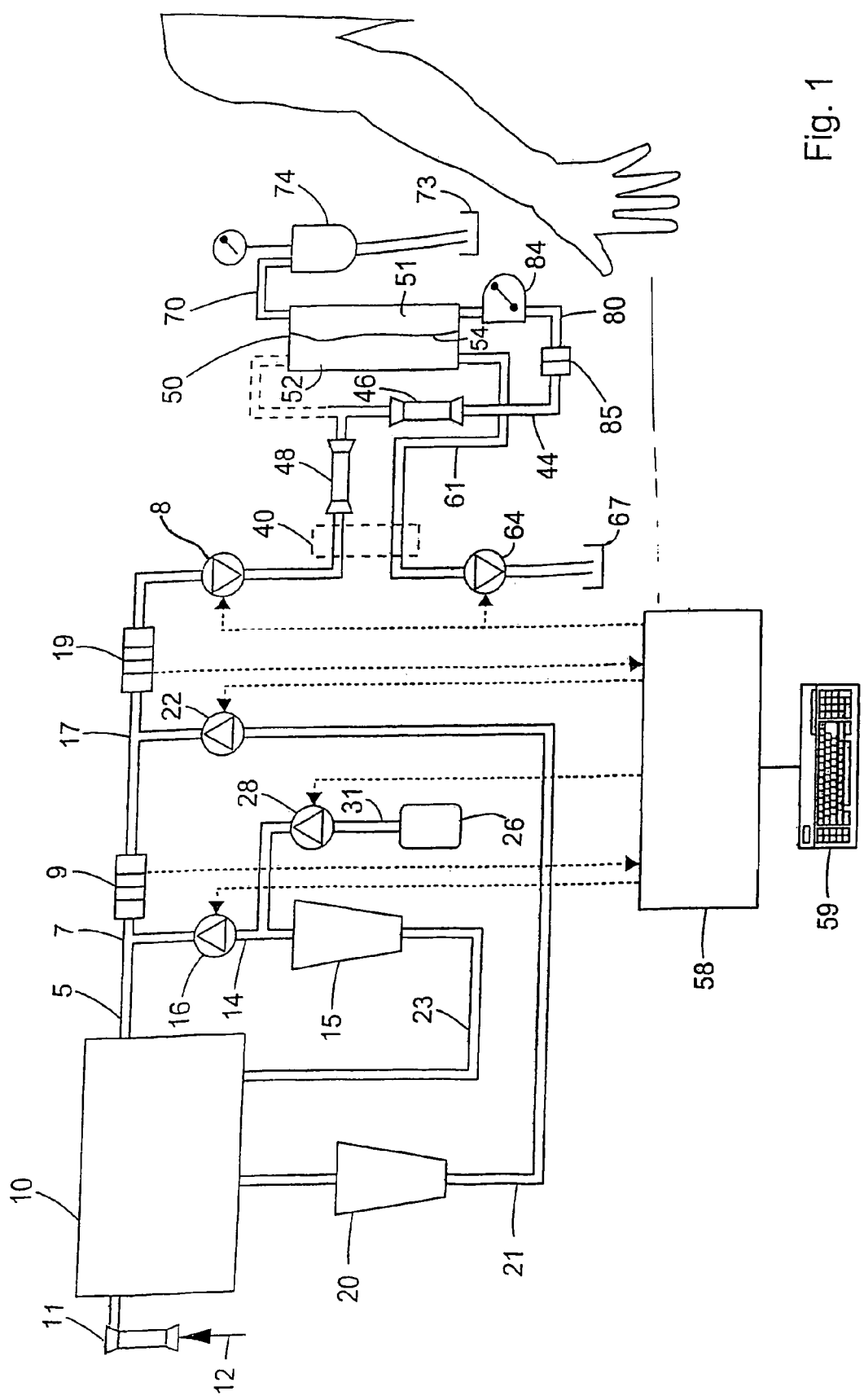
FIG. 1 is a schematic diagram of a dialysis machine according to the invention.

The general term dialysis as used here includes hemodialysis, hemofiltration, hemodiafiltration and therapeutic plasma exchange (TPE), among other similar treatment procedures. The general term dialyzer as used here includes hemofilters and hemodiafilters amongst other similar devices. The general term saline solution as used here includes any solution comprising saline, preferably a substantially physiological saline solution. In general, solutions comprising saline, described as substantially physiological saline solutions, are approved by the health and/or regulatory authorities in the country in which they are used. Therefore, these saline solutions comprising saline may differ somewhat in their composition in different countries, but a physiologically acceptable saline solution is always a solution that is physiological acceptable used, or when administered to a patient. An example of an acceptable physiological saline may be a solution comprised of about 0.85% salt and distilled water; this solution approximately, therefore, being equal to the salt content of blood serum and thereby able to maintain normal osmotic pressure in the body. The term saline solution as used here also includes in any solution containing minor amounts of other electrolytes and other components such as those normally used in preparing for the dialysis liquid, and can include, for example, potassium, calcium, magnesium, glucose and/or acid, as long as the solution remains substantially physiological: a typical solution with a sodium ion concentration may contain, for example, about 154 mmol/l. Deviations from this concentration in the range of 150 to 158 mmol/l are tolerable.

In FIG. 1, a dialysis machine according to a first preferred embodiment of the invention includes a dialyser 50 having two compartments 51 and 52 that are separated by a semipermeable membrane 54. The compartment 51 is connected to a circuit for convening a flow of blood outside the body of a patient comprising an upstream duct 80, usually referred to as arterial line, having a peristaltic pump 84 disposed therein, and a downstream duct 70, usually referred to as venous line. Venous line 70 is provided with a bubble trap 74 and the free ends of the ducts of the arterial and venous lines can be fitted respective needles or catheter connections to enable them to be connected to the vascular circuit of a patient.

The dialysis machine comprises a system for preparing dialysis fluid from dialysate fluid concentrate and/or powder including a heating reservoir 10 having an inlet 12 for water from for example a reverse osmosis unit. An ultra filter 11 is placed between the water inlet 12 and the tank 10. A dry powder vessel 20 containing bicarbonate is disposed in duct 21. A part of the water in the heating reservoir 10 is flown through the vessel 20 by a precisely controlled pump 22. Thus, a saturated bicarbonate solution is obtained from the vessel 20, and mixed into the main duct 5 at mixing point 17. The dialysis fluid preparation system further comprises a duct 23 for preparing sodium chloride concentrate. A dry powder vessel 15 containing sodium chloride is disposed in duct 23. A part of the water in the heating reservoir 10 is flown through the vessel 15 by a precisely controlled pump 16. Pump 16 is connected to the vessel 15 by a duct 14. Thus, a saturated sodium chloride solution is obtained from the vessel 16 and mixed into the main duct, 5 at mixing point 7. The remaining electrolytes used in dialysis fluid, e.g. potassium, calcium, magnesium, and other substances such as glucose and acid are added into duct 5 at mixing point 7 by withdrawing a concentrate solution containing from a small bag or canister 26 by means of a metering pump 28 in duct 31.

Pumps 16, 22 and 28 are controlled by a control unit 58. Downstream of mixing points 7 and 17 conductivity cells 9 and 19 monitor the conductivity change caused by the introduction of the respective electrolytes in the main duct 5. The signal of the respective conductivity cell is in a closed loop manner compared with the expected conductivity determined by the control unit 58. When the actual conductivity differs from the expected the control unit 58 adjusts the respective pump 16 and 22 in order to arrive at the correct conductivity and composition of the dialysate fluid.

The main duct includes a pump 8 and in normal dialysis operation (not shown) directs the dialysate fluid to an inlet of compartment 52 of the dialyser 50. During normal dialysis operation, an outlet of the compartment 52 is connected to a downstream duct 61 having an extraction pump 64 disposed therein for establishing variable suction inside the compartment 52. The duct 61 leads to a waste liquid (ultrafiltrate and/or processed dialysis liquid) container 67. Duct 5 leading to compartment 52 and duct 61 leading away from compartment 52 both pass a flow rate cell 40.

The dialysis machine is provided with input means 59 allowing an operator to select a mode of operation in which the dialysis machine prepares a saline or a saline like solution. In this mode of operation pumps 22 and 28 are not operated. The conductivity set value for the conductivity cell 9 downstream of mixing point 7 is set to a value corresponding to a solution having a sodium chloride concentration of 154 mmol/l and pump 16 is controlled accordingly.

For priming the extracorporeal circuit, an infusion line 44 is connected to the main duct 5. The main duct 5 comprises a second ultrafilter 48. The infusion line 44 includes another ultrafilter 46 for ensuring the sterility of the fluid delivered. There are thus three ultrafilters in series to guarantee sufficient sterile quality of the priming fluid by removing bacteria and endotoxins. Fewer ultrafilters may be used, however with an increased risk of insufficient sterility of the replacement fluid. The infusion line 44 is primed with the saline solution and then the infusion line is connected to the arterial bloodline 80 by connector 85 and the priming of the extracorporeal circuit begins. The venous bloodline 70 is typically connected to a waste bag 73 or another type of drain connection.

Once the extracorporeal circuit is sufficiently primed, the patient can be connected. According to a preferred embodiment, the control unit 58 of the dialysis machine is connected to a sensor (not shown) that detects the presence of blood in the extracorporeal blood circuit. The control unit 58 adjusts the settings of the pumps 16, 22 and 28 and the conductivity cells 9 and 19 to values for preparing dialysate fluid with a composition in accordance with the settings of the operator. The usual setting for sodium ions is for instance 140 mmol/l and the usual setting for bicarbonate ions is 34 mmol/l.

After the treatment is completed, the infusion line is connected to the arterial bloodline again whilst the venous bloodline remains connected to the patient (not shown) the control unit 58 sets the pumps 16, 22 and 28 for preparing a saline solution and by means of pump 8 the saline solution is transported into the extracorporeal circuit to rinse back the patient blood.

According to a preferred embodiment, the saline solution is produced by mixing sodium chloride concentrate coming from vessel 15 and the concentrate of vessel 26 with the water in the main duct 5. The resulting saline solution will, apart from sodium chloride, contain some minor amounts of other electrolytes and some acid, but this does not pose any problem for the patients.

According to a preferred embodiment, chamber 52 of the dialyser is also filled with the saline solution. Hereto chamber 52 is connected to the main duct 5 as in the dialysis treatment (not shown), and the saline solution is pumped into chamber 52.

Before beginning the preparation of the saline solution, the vessel 15 containing sodium chloride in dry form, is primed by drawing water in from heating vessel 10 though activation of pump 16. Line 31 is primed by running pump 28 at high speed until a fluid flow is detected. The vessel 20 containing sodium bicarbonate does not have to be primed until the patient is connected. If it is primed anyway before the saline preparation has started, the main duct 5 is rinsed from bicarbonate before the saline preparation begins.

The vessels 15 and 20 containing the electrolytes in dry form do not necessarily have to be cartridges as shown in the accompanying drawings. Bags, or any other kind of containers are equally suitable.

The fluid preparation system does not have to be based on the use of a flow rate cell 40. The present invention will operate also with fluid preparation systems using the balance chamber principle.

Further it has been shown above to start with sodium chloride in dry form. Of course, it is also possible to use sodium chloride concentrate instead.

The invention claimed is:

1. A method of priming or rinsing back an extracorporeal circuit using a dialysis machine comprising a dialysis liquid preparation system having, a source of water, separate sources of bicarbonate concentrate and sodium chloride concentrate, said extracorporeal circuit comprises an arterial line, connectable to a patient, for drawing blood from the patient, a venous line, connectable to the patient, for returning the blood to the patient, and a blood side compartment of a dialyser, said method comprising the steps of:
preparing a saline solution from said source of water and said source of sodium chloride concentrate to obtain a saline solution, wherein bicarbonate is absent from the saline solution;
connecting said arterial line to an outlet of the dialysis liquid preparation system of the dialysis machine by means of a coupling during priming; and
filling the extracorporeal circuit with said saline solution, wherein said saline solution is conducted from the outlet of the dialysis liquid preparation system of the dialysis machine to the arterial line.

2. A method according to claim 1, further comprising the step of preparing said sodium chloride concentrate by dissolving sodium chloride in water.

3. A method according to claim 2, wherein said arterial line is connected to the dialysis machine through an infusion line and includes an ultrafilter.

4. A method according to claim 1, wherein the saline solution further comprises minor amounts of other electrolytes and other components for the dialysis liquid, said electrolytes and other components being selected from the group of potassium, calcium, magnesium, and glucose with or without acid.

5. A method according to claim 1, wherein the dialysis machine includes a main fluid path, further comprising the steps of priming the main fluid path with said saline solution and filling a dialysis liquid compartment of the dialyser.

6. A method according to claim 3, further comprising the steps of connecting the venous line to a waste bag or other type of drain connection and then starting to fill the extracorporeal circuit beginning with the arterial line.

7. A method according to claim 1, comprising the step of passing the water from said source of water and/or said saline solution from said source of water and said source of sodium chloride concentrate through one or more ultrafilters for removal of bacteria and endotoxins.

8. A method according to claim 6, further comprising the step of providing an indication that the dialysis machine is ready for filling said extracorporeal circuit prior to the step of starting to fill the extracorporeal circuit.

9. A method according to claim 1, wherein the saline solution is substantially physiological with a sodium ion concentration about 154 mmol/l.

10. A method according to claim 6, wherein the sodium ion concentration is lowered from about 154 mmol/l to about 140 mmol/l and the bicarbonate ion concentration risen from about 0 mmol/l to about 34 mmol/l after priming is completed.

11. A method according to claim 3, wherein the infusion line is connected to a main duct of the dialysis liquid preparation system.

12. A method according to claim 11, wherein the main duct comprises an ultrafilter.

* * * * *